(12) United States Patent
Birgersson

(10) Patent No.: US 8,649,525 B2
(45) Date of Patent: Feb. 11, 2014

(54) SYSTEM FOR HEARING PROTECTORS

(75) Inventor: Joakim Birgersson, Vetlanda (SE)

(73) Assignee: MSA Sordin AB, Varnamo (SE)

( * ) Notice: Subject to any disclaimer, the term of this patent is extended or adjusted under 35 U.S.C. 154(b) by 615 days.

(21) Appl. No.: 12/679,504

(22) PCT Filed: Sep. 24, 2008

(86) PCT No.: PCT/SE2008/000525
§ 371 (c)(1),
(2), (4) Date: Apr. 7, 2010

(87) PCT Pub. No.: WO2009/041873
PCT Pub. Date: Apr. 2, 2009

(65) Prior Publication Data
US 2010/0189277 A1    Jul. 29, 2010

(30) Foreign Application Priority Data

Sep. 28, 2007  (SE) .................................. 0702180

(51) Int. Cl.
*G10K 11/16*   (2006.01)
*H03B 29/00*   (2006.01)
*A61F 11/06*   (2006.01)

(52) U.S. Cl.
USPC .......................................... 381/71.6; 381/72

(58) Field of Classification Search
USPC ..................... 381/72, 71.6, 74, 309
See application file for complete search history.

(56) References Cited

U.S. PATENT DOCUMENTS 3,952,158 A  *  4/1976  Kyle et al. ...................... 381/72
2004/0258253 A1 * 12/2004 Wurtz ........................ 381/71.6
2005/0238181 A1   10/2005 Nilsson et al.

FOREIGN PATENT DOCUMENTS

DE          101 17 705 A1    10/2001

OTHER PUBLICATIONS

International Preliminary Report on Patentability, dated Mar. 30, 2010 to corresponding international patent application No. PCT/SE2008/000525, filed Sep. 24, 2008, 6 pages.
International Search Report dated Jan. 30, 2009 to corresponding international patent application No. PCT/SE2008/000525, filed Sep. 24, 2008, 3 pages.

\* cited by examiner

*Primary Examiner* — Ping Lee
(74) *Attorney, Agent, or Firm* — Maier & Maier, PLLC

(57) ABSTRACT

A system for hearing protection comprising an outer hearing protection unit, an inner hearing protection unit, and an outer microphone is disclosed, the inner hearing protection unit comprising a speaker and the microphone being arranged to be electrically connectable for transmission of signals to the speaker.

11 Claims, 1 Drawing Sheet

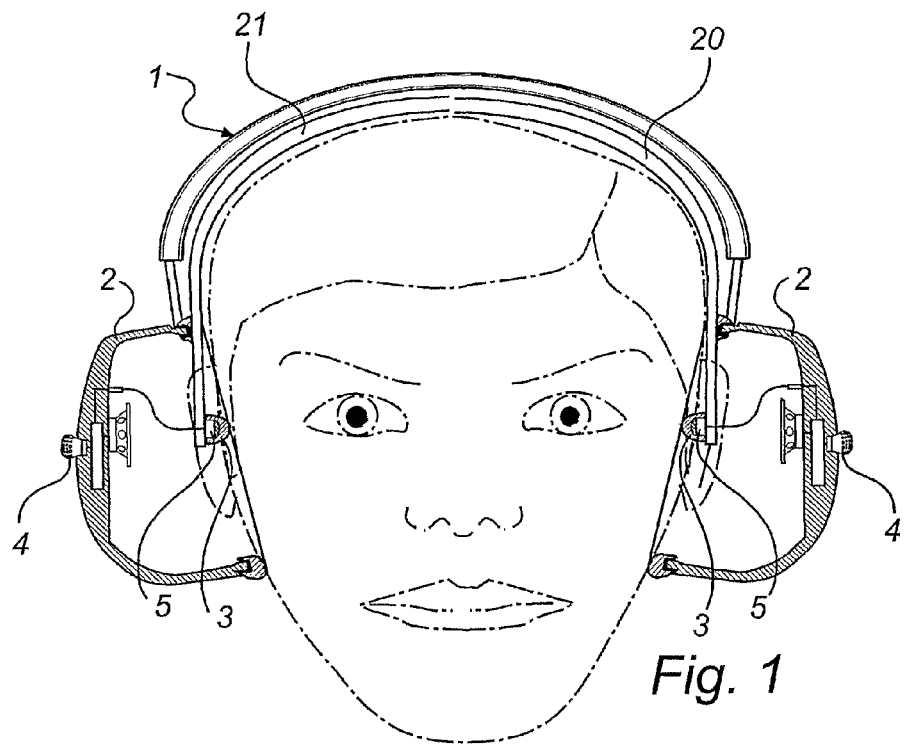
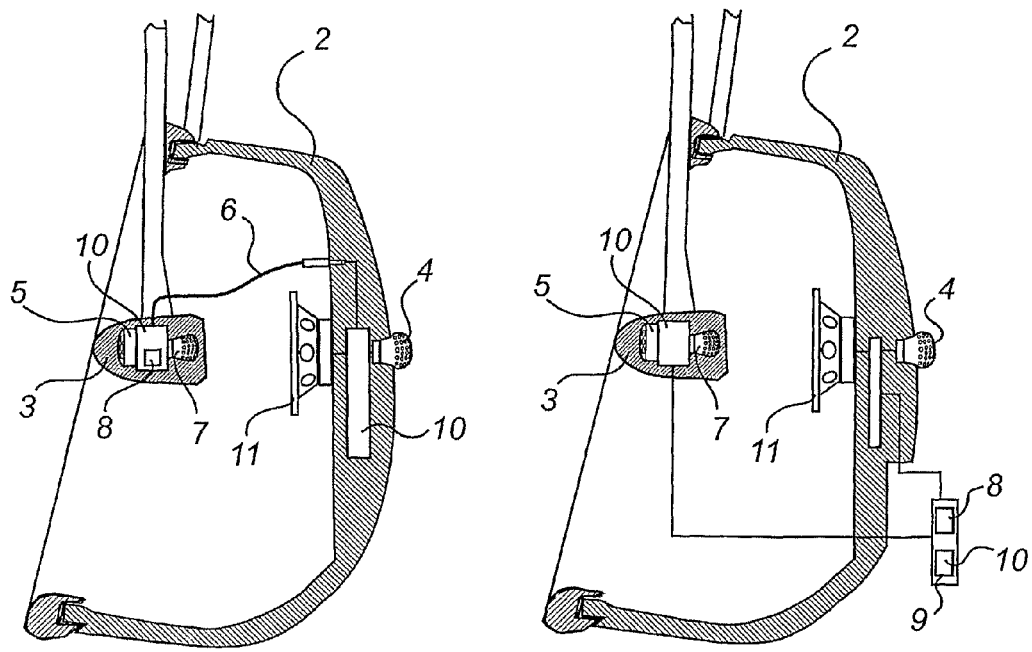

SYSTEM FOR HEARING PROTECTORS

RELATED APPLICATIONS

This application claims priority, under 35 U.S.C. §119, to international patent application No.: PCT/SE2008/000525, filed on Sep. 24, 2008, which claims priority to Swedish patent application No.: 0702180-1, filed Sep. 28, 2007, the disclosures of which are incorporated by reference herein in their entireties.

TECHNICAL FIELD

The present document relates to hearing protection systems. More specifically, the present document relates to a system for hearing protection according to the preamble of claim 1, and to an ear cup and an ear plug for use in such a system.

BACKGROUND ART

Two main types of hearing protectors are hearing protectors with ear cups and hearing protectors with ear plugs. Ear cups are intended to be positioned over the ears of a wearer and are usually secured by a headband, which runs partly around the wearer's head and which interconnects the hearing protectors. Ear plugs are intended to be positioned in the auditory canal and may also be secured by a corresponding headband.

Traditional hearing protectors comprise a sound-attenuating material, a sound absorber, which separates the inner parts of the ear from the surroundings. The purpose of the sound absorber is to prevent harmful noise from reaching the inner parts of the ear, for example the eardrum. Hearing protectors of this kind are called passive, since they attenuate all ambient sounds to the same degree over time.

In addition, more modern hearing protectors may comprise electronic circuitry that picks up ambient sounds through a microphone, converts them to appropriate levels and/or filters out the desired sound content and plays it back to the user by means of a speaker contained in the hearing protector. Hearing protectors of this kind are called active hearing protectors, because they contain, contrary to passive hearing protectors, active components.

Accordingly, a conversion of the sound occurs in active hearing protectors: first, the sound signal picked up by the microphone is converted to an electric signal for further signal processing, and then a sound signal is reproduced for the purpose of playing it back to the user through a speaker facing the user's ear.

One type of active hearing protector is a level-dependent hearing protector, which comprises an electronic circuit designed to adapt the sound pressure level. Such hearing protectors protect the user, for instance, by filtering out impulse noise, such as gunshots, from the surroundings, and/or by continuously adapting all ambient sound received to an appropriate level before it is reproduced to the user.

Active hearing protectors may be essential to allow communication in noisy environments and/or environments where the noise levels vary considerably, or where high impulse sounds might cause hearing damage. In this context, 'communication' may mean, for instance, that a person wearing a hearing protector needs to hear ambient sounds, such as machine sounds or speech, while being protected from harmful noise levels. Active hearing protectors featuring level adaptation are used, for example, in connection with airport operations and hunting.

In many applications either ear cups or ear plugs are used. However, in particularly noisy environments, such as in a helicopter or a tank, it may be advantageous to use both ear plugs and ear cups at the same time.

In these situations, where an active hearing protector is desirable, it is common to use either active ear plugs and passive ear cups or the opposite. Another alternative is to use double active hearing protectors. This implies, however, several conversions of the sound signal and, thus, increased distortion of the reproduced sound.

Using an active cup over a passive plug or an active plug inside a passive cup means that the user will have problems communicating with his surroundings. This is because all sounds, also the desired sounds, are attenuated by the passive protector to a level that makes communication more difficult or even impossible. If, for example, the user wears active ear cups in order to obtain satisfactory monitoring of ambient sounds, and supplements the protection with ear plugs, the level-adapted sound reproduced by the active cups will be further attenuated by the plugs to an extent where it is difficult to make out what is being said.

There is thus a need for an active hearing protector, which can offer sufficient noise attenuation in particularly noisy environments, while providing satisfactory sound quality for sounds reproduced by means of the active protection.

SUMMARY OF THE INVENTION

One object of the present invention is to provide a system for active hearing protection, said system allowing an alternative and/or improved solution to the problem of simultaneous use of two separate hearing protectors, such as ear plugs and ear cups.

A further object of the present invention is to provide improved sound quality when monitoring ambient sounds.

The present invention is based on the understanding that it is advantageous to make only one conversion of the acoustic signal to an electric signal in systems with double hearing protectors and active function.

These objects are achieved entirely or in part by a system for hearing protection comprising an outer hearing protection unit, an inner hearing protection unit, and an outer microphone arranged in connection with the outer hearing protection unit, the inner hearing protection unit comprising a speaker and the microphone being arranged to be electrically connectable for transmission of signals to the speaker.

By 'outer hearing protecting unit' and 'inner hearing protection unit' is meant hearing protectors that are separable from one another and that may be positioned, when used simultaneously, so that the inner hearing protection is located substantially inside the outer hearing protection relative to the eardrum of the user. This does not exclude, however, the possibility of some part of the inner hearing protection unit, when used in this way, being located outside some part of the outer hearing protection unit.

By 'microphone' is meant, according to the usual definition, a sound conversion unit for converting an acoustic signal in the form of pressure waves in the air to an electric signal.

By 'outer microphone' is meant that the microphone is arranged to pick up ambient sound and is located on the outside of the hearing protection system, for example integrated into/mounted on the outer hearing protection unit, or any other appropriate part of the system. Thus, it is possible for the outer microphone to be arranged, for example, in a headband, an integration unit or an adapter forming part of the hearing protection system.

Correspondingly, by 'speaker' is meant a conversion unit that converts an electric signal to an acoustic signal in the form of pressure waves in the air.

An advantage of the system is that, in addition to double passive attenuation of ambient sound, it also offers an active protection, which allows the user to communicate with his surroundings, since the active function of the system ensures that desired sounds may be picked up by the outer hearing protection unit and reproduced to the user via the inner unit, so that speech, for instance, becomes audible despite the double attenuation.

A further advantage of such a system is that the sound is converted to electrical signals and back again to acoustic signals only once, whereby distortion is reduced compared with conventional, non-integrated active cups and active plugs, which, when used simultaneously, cause distortion by the sound being converted from an acoustic signal to an electric signal and back again in each of the hearing protection units (the active cups and the active plugs). These double conversions may cause distortion and reduce the sound quality, which makes it difficult to understand the communication received.

The system may comprise an integration unit arranged for transmission of an electric signal generated in the microphone to the speaker.

The inner hearing protection unit may comprise a microphone for picking up ambient sound.

An advantage thereof is that the inner hearing protection unit may be used as an active hearing protector also when being used separately. Thus, if say the noise level drops, a user may choose to use only the inner protector in the form of, for example, active ear plugs.

The system may comprise a microphone switch for switching on and switching off the microphone of the inner hearing protection unit.

The system may comprise a detector arranged to detect when the integration unit is connected for the purpose of conducting an electric signal generated in the outer hearing protection unit to the inner hearing protection unit, and in response thereto switch off the microphone of the inner hearing protection unit.

This enables simultaneous use of active ear cups and active ear plugs in the system in a user-oriented and flexible manner. Such a system with two integrable and separable active hearing protection units, such as active cups and active plugs, offers reduced distortion and improved quality of the sound reproduced to the user, while providing double noise attenuation. For a user working in, for instance, an industrial environment, not having to manually adjust the equipment for simultaneous use of the two active protectors may be useful.

The integration unit may comprise an adapter which has an inlet for each of the two hearing protection units and which may be arranged to detect when both hearing protection units are connected.

The adapter may be arranged in a separate unit.

The adapter may be arranged to switch off the microphone of the inner hearing protection unit in response to detecting connection of both hearing protection units.

The integration unit may be a conductor.

This enables user-oriented integration of the respective hearing protection units to obtain an active protection.

The system may comprise a signal adaptation circuit arranged to adapt the electric signal produced by the microphone such that a desired acoustic signal is emitted by the speaker.

The signal adaptation circuit may be arranged in the outer hearing protection unit.

The signal adaptation circuit may be arranged in the inner hearing protection unit.

The signal adaptation circuit may be arranged in the integration unit.

The outer hearing protection unit may comprise a speaker for playing back an acoustic signal.

This has the advantage of allowing the use of an active cup in the system, which cup may also be used separately.

The microphone may be arranged in connection with the outer hearing protection unit.

This means that the microphone is arranged in and/or on the outer hearing protection unit, which may be advantageous if this unit is to be used separately. As another example, the microphone may be mounted in another unit which is so arranged, for instance in an adapter or an integration unit, that its location is suitable for picking up ambient sound.

According to a second aspect of the present invention, an ear cup and/or an ear plug adapted for use in a system as described above is provided.

BRIEF DESCRIPTION OF THE DRAWINGS

Further advantages and embodiments of the present invention will be apparent from the following detailed description and the appended drawings, on which:

FIG. 1 is an overall, schematic front view of a system for hearing protection according to the present invention;

FIG. 2 is a schematic sectional view of a part of a first embodiment of a system for hearing protection according to the present invention.

FIG. 3 is a schematic sectional view of a second embodiment of a system for hearing protection according to the present invention.

DETAILED DESCRIPTION OF EMBODIMENTS

FIG. 1 is an overall, schematic and partial sectional front view of a system 1 for hearing protection according to the present invention, as arranged on the head of a user. The system 1 comprises an outer hearing protection unit 2 in the form of a pair of ear cups and an inner hearing protection unit 3 in the form of a pair of ear plugs. Two headbands 20, 21 are arranged to interconnect the respective pairs and allow a comfortable fit on the user's head. Both the ear cups 2 and the ear plugs 3 comprise a sound-absorbing and/or sound-insulating material, which serves to attenuate ambient sound before it reaches the inner ear of the user. The system 1 is also adapted to provide an active hearing protector by the ambient sound being picked up by a microphone 7 mounted in the respective ear cup 2 and adapted to convert the acoustic sound signal in the form of pressure waves to an electric signal, which may be processed using current technology to provide a desired signal, for example by level adaptation or frequency filtering. The desired electric signal thus obtained is then conducted via an integration unit 6, here in the form of a conductor, to a speaker 5 in the ear plug 2 for reproduction of a desired acoustic signal that is played back to the user.

Owing to the electric connection between the microphone 4 of the ear cup 2 and the speaker 5 of the ear plug 3 only one conversion occurs from an acoustic signal to an electric signal and back again. In this way, no unnecessary distortion is added because of double sound conversions, and excellent sound quality of the reproduced sound can be obtained, while ensuring efficient noise attenuation.

FIG. 2 is a schematic sectional view illustrating in more detail a part of a further embodiment of a system 1 for hearing protection according to the present invention.

The figure illustrates an active ear cup 2, which in itself comprises means for picking up an acoustic sound signal and converting it to an electric signal in a microphone 4, a signal adaptation circuit 10 for signal processing and generation of a desired signal, and a speaker 11 for converting a desired signal to an acoustic signal that is audible to the user. The active ear cup 2 is adapted for use in a system 1 for hearing protection according to the present invention by the microphone 4 being arranged to be electrically connectable, by means of the integration unit 6 in the form of a conductor, for transmission of signals to the speaker 5 of an inner hearing protection unit 3 in the form of an ear plug, which in a corresponding manner constitutes in itself an active hearing protector, which, in addition to the speaker 5, also comprises a microphone 7 and a signal adaptation circuit 10.

When the integration unit 6 is connected, it conducts sound signals, after they have been picked up in the form of acoustic signals from the surroundings and converted to electric signals by the microphone 4 and subsequently adapted in the adaptation unit 10, from the ear cup 2 to the ear plug 3, where the desired signals are converted to audible acoustic signals and played back to the user via the speaker 5.

The figure illustrates, also schematically, a microphone switch 8, which is arranged to switch on/off the microphone 7 of the ear plug 3. The switch may be a manual switch or, alternatively, the system may comprise a detection unit which detects when the integration unit 6 is connected, in which case the microphone 7 is automatically switched off.

FIG. 3 illustrates a further embodiment of a system 1 for hearing protection according to the present invention, with an outer hearing protection unit 2 in the form of an ear cup and an inner hearing protection unit 3 in the form of an ear plug. The ear cup and the ear plug 2 and 3, respectively, form separate active hearing protectors, each comprising a microphone 4 and 7, respectively, a signal adaptation circuit 10 and a speaker 11 and 5, respectively. In this system, the integration unit also comprises an adapter 9 having inlets for connection of the ear cup 2 and the ear plug 3, respectively. The adapter 9 comprises a microphone switch 8 and a signal adaptation circuit 10.

When the two active hearing protection units 2, 3, i.e. the active ear cups and the active ear plugs, are interconnected ambient sound is picked up and converted to an electric signal by the microphone 4, whereupon the signal is supplied to the adapter 9. The adapter 9 detects whether both the ear cup 2 and the ear plug 3 are connected, produces a desired signal by means of the signal adaptation circuit 10 and switches off the microphone 7. The desired signal is supplied to the ear plug 3 and is converted by the speaker 5 to an acoustic signal and played back to the user.

It will be appreciated by a skilled person that several of the components of the system, such as the signal adaptation circuits, switches and detectors, may be arranged in the system in ways other than those represented in the figures. For example, signal adaptation circuits may be provided both in the hearing protection units and in the adapter and/or in the integration unit, or only in one or some of these units. Combined and/or separate signal adaptation circuits may be arranged in two or more of the units of the system.

According to one embodiment, no switching off of the microphone 7 occurs when using double hearing protectors.

The system may be formed of hearing protection units which each constitute active hearing protectors, such as the active ear cups and ear plugs shown in FIGS. 2 and 3. However, the hearing protection units may also be adapted, in one embodiment, to provide active protection only when combined in a hearing protection system. In this case, no external speaker is required, for example, in the outer hearing protection unit 2, and/or no microphone is required in the inner hearing protection unit 3.

The integration unit may be a conductor in the form of a wire, as shown in FIGS. 1 and 2. In another embodiment, the integration unit may be an adapter that is connectable to the respective hearing protection units via wires, as shown in FIG. 3, and in yet another embodiment the integration unit may be a device for wireless communication between the hearing protection units.

The signal adaptation circuit may be of the type that filters out certain frequencies and/or reproduces ambient sound at a level that is appropriate for the user.

When using the system, the sound-attenuating part of the inner hearing protection unit may be located completely inside the sound-attenuating part of the outer hearing protection part, if by 'sound-attenuating part' is meant the part of the hearing protection unit that is formed of a sound-attenuating material. This does not exclude, however, the possibility of some parts of the inner hearing protection unit, such as the headband and/or other parts, being located outside the outer unit.

To further improve the communication conditions, the microphone of the outer unit may be adapted to be directable towards a desired sound source, such as a speaker or a machine.

Furthermore, the system may be adapted for two-way communication by comprising, or being integrable with, for example a communication radio. The communication radio may be integrable with, or arranged in, an adapter. In this case, a 'push to talk'-button may be integrated in some part of the system, such as the adapter.

The microphone may be provided in the outer hearing protection unit, or arranged in connection thereto, for instance attached to the outside of an ear cup, as in a headset design.

The inner and outer hearing protection units, respectively, may be arranged in pairs and interconnected by, for example, headbands. In one embodiment of the invention, the system has only one headband and the inner and outer hearing protection units, respectively, are both mounted on this one headband. Each of the hearing protection units may, in one embodiment, be adapted to be mounted adjacent the ear of a user by means of separate mounting means that do not extend between the two hearing protection units of a pair.

The inner hearing protection units, for instance when consisting of ear plugs, may be designed such that they can be arranged in a user-friendly manner completely or partly inside the auditory canal of the user. This can be achieved with or without additional mounting means.

In yet another embodiment, the inner and/or outer hearing protection units may be arranged on and/or in a headgear, such as a helmet.

The outer hearing protection units may, optionally, be designed to be worn over the ears and the inner hearing protection units may, optionally, be designed to be worn completely or partly inside the auditory canal of the user.

The invention claimed is:

1. A system for hearing protection comprising an outer hearing protection unit, an inner hearing protection unit, and an outer microphone arranged in connection with the outer hearing protection unit, the inner hearing protection unit further comprising a speaker, wherein the microphone is arranged to be electrically connectable for transmission of signals to the speaker, wherein the inner hearing protection unit further comprises a microphone for picking up ambient sound, the system further comprising an integration unit arranged for transmission of an electric signal generated in the outer microphone to the speaker, wherein the integration unit further comprises an adapter with an inlet for each of the two hearing protection units, said adapter being arranged to detect when both hearing protection units are connected, wherein the adapter is arranged to switch off the microphone of the inner hearing protection unit in response to detecting connection of both hearing protection units.

2. A system for hearing protection according to claim 1, wherein the system further comprises a microphone switch for switching on and switching off the microphone of the inner hearing protection unit.

3. A system for hearing protection according to claim 2, further comprising a detector arranged to detect when an integration unit is connected for the purpose of conducting an electric signal generated in the outer hearing protection emit to the inner hearing protection unit, and in response thereto switch off the microphone of the inner hearing protection unit.

4. A system for hearing protection according to claim 1, wherein the adapter is arranged in a separate unit.

5. A system for hearing protection according to claim 1, wherein the integration unit is a conductor.

6. A system for hearing protection according to claim 1, comprising a signal adaptation circuit arranged to adapt the electric signal produced by the microphone such that a desired acoustic signal is emitted by the speaker.

7. A system for hearing protection according to claim 6, wherein the signal adaptation circuit is arranged in the outer and/or the inner hearing protection unit.

8. A system for hearing protection according to claim 6, wherein the signal adaptation circuit is arranged in an integration unit arranged for transmission of an electric signal generated in the microphone to the speaker.

9. A system for hearing protection according to claim 1, wherein the outer hearing protection unit comprises a speaker for playing back an acoustic signal.

10. A system according to claim 1, further comprising an ear cup.

11. A system according to claim 1, further comprising an ear plug.

* * * * *